United States Patent [19]

Marden

[11] 4,064,401
[45] Dec. 20, 1977

[54] HEADHOLDER ASSEMBLY

[76] Inventor: Danny Alden Marden, 5005 Fillmore Ave., No. 10, Alexandria, Va. 22311

[21] Appl. No.: 654,998

[22] Filed: Feb. 4, 1976

[51] Int. Cl.² .................................... H01J 37/20
[52] U.S. Cl. ............................................ 250/456
[58] Field of Search .......... 250/446, 451, 456, 445 T, 250/439 P, 491; 297/410, 392

[56] References Cited

U.S. PATENT DOCUMENTS

| 1,134,720 | 4/1915 | Bradley | 297/392 |
| 2,032,833 | 3/1936 | Broadbent | 250/456 |
| 3,655,968 | 4/1972 | Moore et al. | 250/451 |

Primary Examiner—Bruce C. Anderson
Attorney, Agent, or Firm—Morland Charles Fischer

[57] ABSTRACT

An improved assembly is disclosed to orient and immobilize the head of a patient for the purpose of taking x-ray pictures. The size of the assembly is adjustable to readily fit different patient accomodating means (e.g. a table, chair or the like). The assembly is free to move in any of a plurality of directions in order to conveniently engage the head of the patient. The assembly can be moved out of the way of the patient so as to allow easy access to or exit from the patient accomodating means.

8 Claims, 7 Drawing Figures

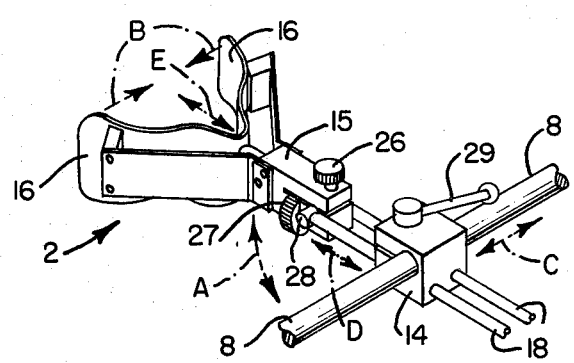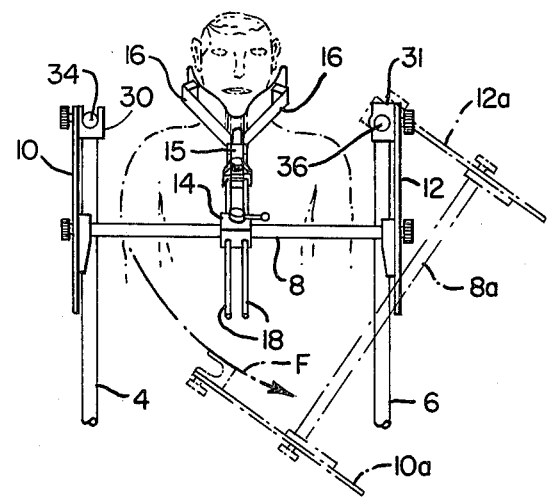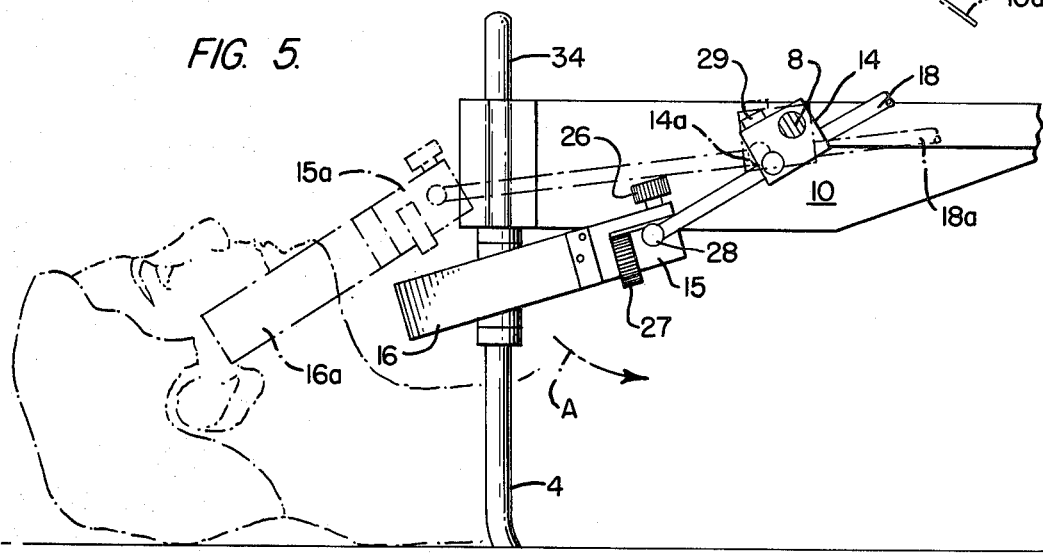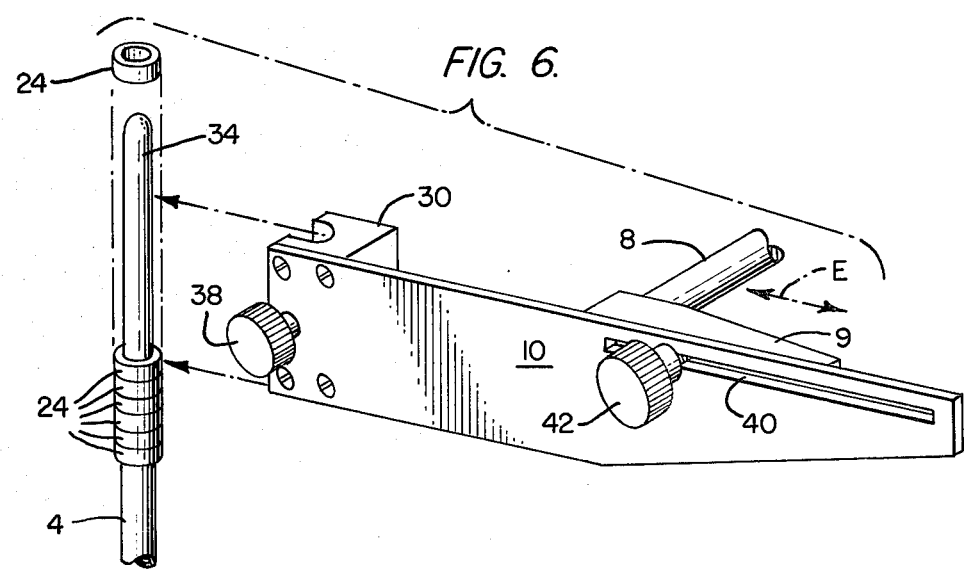

HEADHOLDER ASSEMBLY

BACKGROUND OF THE INVENTION

1. Field of the Invention

This invention relates to an adjustable assembly for securing the head of the patient in a desired position for the purpose of taking x-ray pictures.

2. Prior Art

Examples of conventional support assemblies which orient the head of a patient in a desired position to permit the taking of x-ray pictures include U.S. Pat. Nos. 3,521,057 issued Jul. 21, 1970, and 3,655,968 issued Apr. 11, 1972.

However, the conventional head support assemblies are not adapted to readily fit different patient accomodating means, such as a table, chair, or the like. More particularly, the size of the conventional head support assemblies is not adjustable to correspond to the dimensions of the different patient accomodating means. Moreover, the relative immobility of conventional head support assemblies undesirably increases the difficulty by which to engage and immobilize a patient's head. What is more, the conventional head support assemblies are not generally suitable for use with a CAT (computerized axial tomography) unit.

SUMMARY OF THE INVENTION

Briefly, and in general terms, an improved headholder assembly is disclosed to position and support the head of a patient for the purpose of taking x-ray pictures. The headholder assembly is adapted to fit a patient accomodating means, such as a table, chair or the like. The instant assembly includes side supporting rails which conform to the general configuration of and are fastened to the patient accomodating means. A side plate is connected to the upper end of each support rail. Each side plate has a slot formed therein. A bar is connected between the side plates. The position of the connecting bar is changed by movement thereof relative to the slots in the side plates to affect a corresponding change in the position of the headholder assembly with respect to the head of the patient.

A central clamping block has apertures therein to receive the connecting bar and a pair of elongated chin support extension rods. The rods and the connecting bar extend through the central clamping block in substantially perpendicular directions with respect to one another. The rods are connected at one end thereof to a chin support member which is contoured to fit the face and chin of a patient. The proximity of the chin support member to a patient's head is selectably changed by either moving the extension rods through the central clamping block or by sliding the central clamping block along the connecting bar to a desired location between the side plates.

One of the side plates is adapted to be disengaged from its respective side support rail. The headholder assembly may thereupon be pivoted about the upper end of another support rail so as to enable the patient to gain access to or alight from the patient accomodating means.

BRIEF DESCRIPTION OF THE DRAWINGS

FIG. 3 is a detailed showing of the headholder assembly of the instant invention;

FIG. 4 illustrates the means by which the instant headholder assembly may be pivoted out of the way to permit a patient to gain access to or alight from a patient accomodating means;

FIG. 5 is a showing of one example for advancing the instant assembly into engagement with a patient's head; and FIGS. 6 and 7 are detailed showings of the assembly of the side plates with the support rails and connecting bar of the instant headholder assembly.

DESCRIPTION OF THE PREFERRED EMBODIMENT

Figure 1:
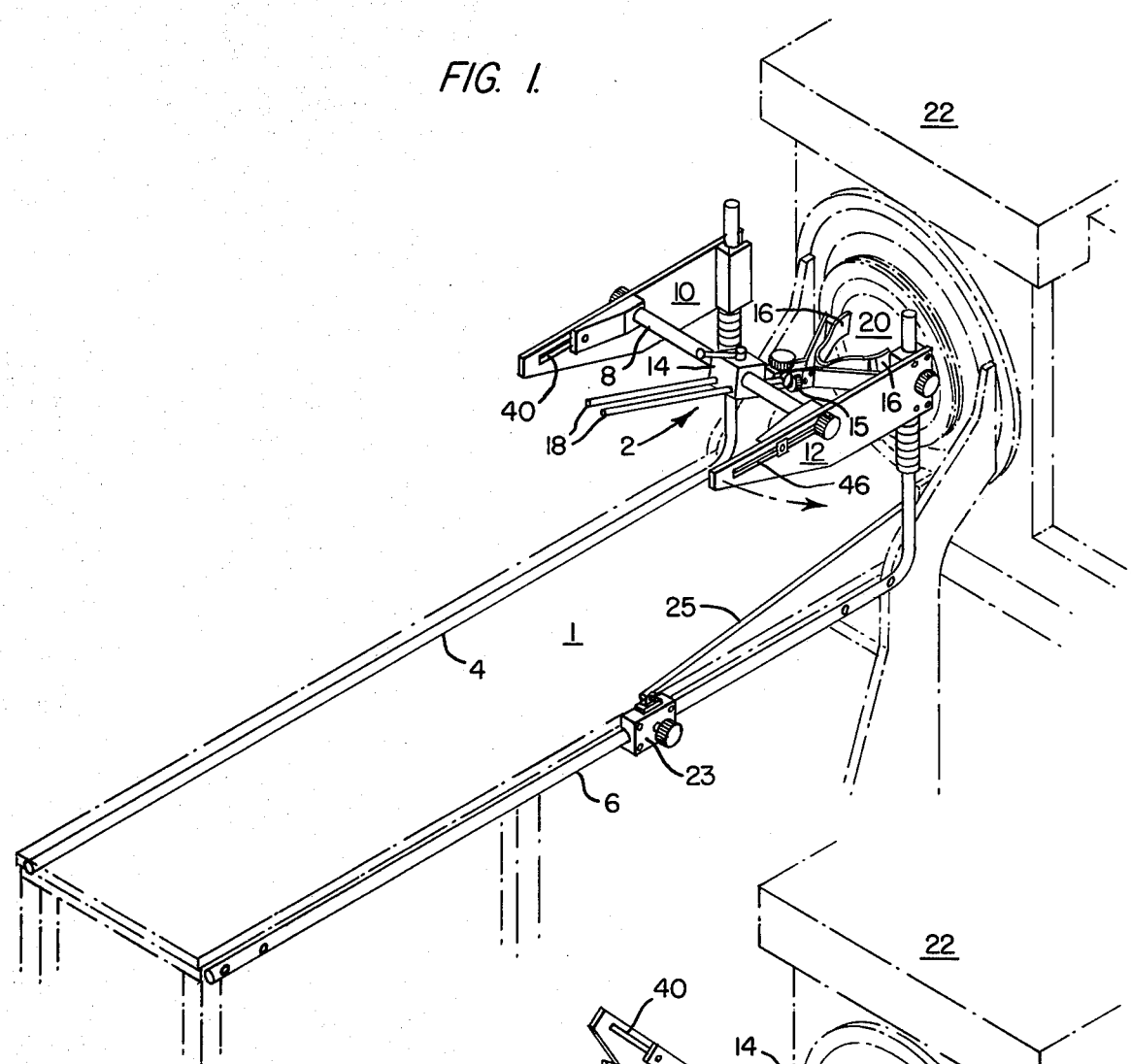
FIG. 1 shows the instant headholder assembly associated with a table.

Referring to FIG. 1, the instant headholder assembly 2 is shown in association with a table 1. The headholder assembly 2 is utilized, for example, to position and support the head of a patient during the taking of x-ray pictures. Side support rails 4 and 6 are secured to respective sides of table 1 by suitable means, such as, for example, bolts. The length and shape of support rails 4 and 6 are determined by the support means used to accommodate the body of a patient. In the present embodiment, a table 1 is employed. Thus, a portion of each support rail 4 and 6 is generally elongated, corresponding in length and shape to table 1. Support rails 4 and 6 stabilize the headholder assembly 2 so as to prevent vibrations, which may occur during the x-ray procedure, from undesirably changing the position of a patient's head.

The assembly 2 includes a pair of side plates 10 and 12. A bar 8 is connected between side plates 10 and 12. One end of connecting bar 8 includes a sleeve portion, the advantage of which will soon become apparent. Side plates 10 and 12 have slots 40 and 46 formed therein. The location of connecting bar 8 may be conveniently changed by movement thereof relative to slots 40 and 46 so as to accordingly change the position of the instant holder assembler 2 in a manner to be shortly described. A central clamping block 14 is provided having suitable apertures formed therein to receive connecting bar 8 and a chin support extension bar means 18. Connecting bar 8 and chin support extension bar means 18 extend through the apertures of central clamping block 14 in substantially perpendicular directions with respect to one another. Central clamping block 14 is adapted to be moved along connecting bar 8 in order to position a chin support member 16 in a convenient location between side plates 10 and 12.

Chin support extension bar means 18, in a preferred embodiment, is comprised of an elongated pair of parallel rods. However, the number of rods which comprise extension bar means 18 is not to be regarded as a limitation of the instant invention. Rods 18 are connected to a chin support control block 15. Chin support control block 15 is connected to the chin support member 16. A suitable portion of the extension rods 18 can be moved through the apertures formed in clamping block 14 to change the portion of chin support member 16 with respect to an x-ray scanner 22. The respective movements of connecting bar 8, clamping block 14, and extension rods 18 relative to one another to effect a desired orientation of the chin support member 16 will be discussed in greater detail hereinafter.

Chin support member 16 is suitably contoured to fit a patient's face and chin and is formed from a soft, comfortable material, such as polyurethane. Chin support 16 may include a strap (not shown) to be connected around the back of a patient'head to prevent movement of the head out of the support.

A patient's head is selectively positioned within a resilient head receiving bag 20 of x-ray scanner 22. The x-ray scanner 22 is included in a computerized axial tomography unit so as to enable the taking of brain scans of a patient's head. The x-ray scanner 23 may rotate 360° around a patient's head in order to expose all areas thereof for panoramic x-ray picture taking. The position of the head receiving bag 20 may be adjusted by means of sliding block 23 and extension bar 25. Extension bar 25 is connected between the rim of the head bag 20 and the sliding block 23. Sliding block 23 has an aperture therein to receive a side support rail. Block 23 is adapted to slide along one of the support rails (e.g. 6) to position head bag 20 as desired.

Figure 2:
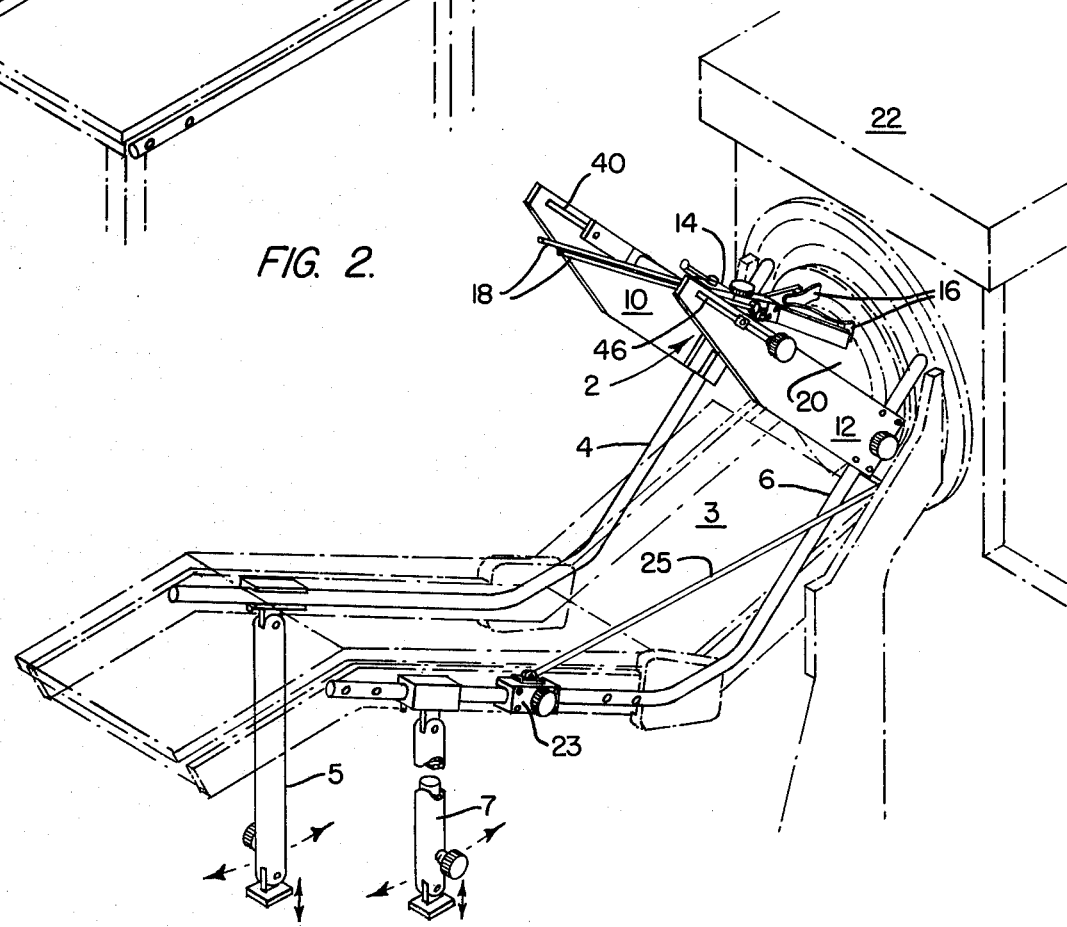
FIG. 2 shows the instant headholder assembly associated with a chair.

The embodiment of FIG. 2 is substantially the same as that shown in FIG. 1, except that the table is replaced by a chair 3, such as that commonly used by a dentist. Side support rails 4 and 6 are generally curved so as to conform to the shape of the chair 3. It is to be understood, however, that the instant headholder assembly is adapted to be utilized in association with any suitable patient accomodating means other than the table and chair shown in FIGS. 1 and 2.

In a preferred embodiment, sliding legs 5 and 7 are respectively attached to support rails 4 and 6. The height and position of legs 5 and 7 with respect to rails 4 and 6 may be adjusted to provide additional support for the rails 4 and 6 and the headholder assembly 2.

FIG. 3 is a detailed showing of the headholder assembly 2 of the instant invention. Chin support control block 15 includes a knob and screw means 26 which engages a restraining bar 28. Restraining bar 28 is inserted through a slot formed in control block 15. One end of each of the extension rods 18 is connected together by restraining bar 28. By suitably adjusting knob and screw means 26 so as to disengage restraining bar 28, control block 15 (and the chin support 16) swivels about bar 28 through an arc, the direction of which is indicated generally by arrow A. Control block 15 also includes a mechanism 27 to adjust the width of the chin support member 16 in a well-known manner (e.g. by a conventional gear train means), as indicated by the arrow B.

Central clamping block 14 further includes a handle 29 to operate a driving screw means, or the like (not shown). The driving screw means precludes movement of connecting bar 8 and the extension rods 18 by clamping bar 8 and rods 18 at respective positions within the apertures of block 14. Handle 29 may be suitably adjusted to loosen the driving screw means. Clamping block 14 and, thus, chin support member 16 may be either rotated in an arc around connecting bar 8 (best shown in FIG. 5) or moved back and forth along connecting bar 8 in a direction indicated generally by arrow C. At the same instance of loosening the driving screw means, rods 18 may also be moved through the apertures in clamping block 14 in order to alter the proximity of chin support member 16 to the x-ray scanner unit, in a direction indicated generally by arrow D. As previously disclosed, the position of the headholder assembly 2 is accordingly changed, in a direction generally indicated by arrow E, by moving connecting bar 8 with respect to the slots provided in the side plates 10 and 12 (best shown and described in FIGs. 6 and 7).

It should be recognized that headholder assembly 2 is effectively provided with a plurality of degrees of freedom in order to accurately position the head of a patient, such as in the head bag of an x-ray scanner. For example, by virtue of the interconnection of the elements which comprise the instant headholder assembly 2, chin support member 16 is adapted to be moved into engagement with a patient's head in any convenient combination of the respective directions generally represented by arrows A, C, and D or E, which directions are in substantially perpendicular planes relative to one another.

Referring to FIG. 4, the side plates 10 and 12 are shown having attached thereto a rail receiving block 30 and a pivot block 31, respectively. The rail receiving block 30 of side plate 10 includes a recessed portion which is adapted to removably receive the upper end 34 of support rail 4 (best shown in FIG. 6). The pivot block 31 of side plate 12 has an aperture therein to receive the upper end 36 of support rail 6 (best shown in FIG. 7). Support rail 4 may be moved out of engagement with rail receiving block 31 so that the side plates 10 and 12 and connecting bar 8 can be pivoted about the upper end 36 of support rail 6 in a direction generally indicated by arrow F. Thus, the side plates and connecting bar are displaced to new positions (i.e. shown dotted and represented by the numbers 10a, 12a and 8a, respectively) to enable a patient to either gain access to or alight from the patient accomodating means.

In operation, FIG. 5 shows one example for advancing chin support member 16 to a suitable position to receive and orient the head of a patient. To achieve such a positioning of chin support member 16, handle 29 is operated so as to cause the driving screw means to unclamp bar 8 from block 14. Clamping block 14 can, thereby, be rotated around connecting bar 8 (to a position designated 14a, shown dotted). Rods 18 are moved through the apertures formed in clamping block 14 toward the location of a patient's head (to a position designated 18a, shown dotted). Knob and screw means 26 is adjusted, and the chin support control block 15 and chin support member 16 are swiveled through a desired arc around bar 28 in the direction generally indicated by arrow A (to respective positions designated 15a and 16a, shown dotted) so as to be aligned with the patient'-face and chin. If necessary, mechanism 27 may be operated to adjust the width of the chin support member 16 to conform to that of the patient's face. Of course, it is to be recognized that the actual order in which clamping block 14, rods 18, and control block 15 are moved to affect the desired positioning of chin support member 16 may be conveniently arranged to suit the operator of the instant headholder assembly.

FIG. 6 is detailed showing of the assembly of side plate 10 with support rail 4 and connecting bar 8. The upper end 34 of support rail 4 is tapered. Safety rings 24 include central holes which are sized to allow the rings to be stacked on the upper end 34 of support rail 4. The safety rings, fabricated of material, such as, for example, aluminum, help to maintain the height of side plate 4 above a patient. As previously disclosed, side plate 10 has attached thereto block 30 which is adapted to removably receive the upper end 34 of support rail 4 in the recessed portion thereof. The upper end 34 of support rail 4 is disengaged from rail receiving block 30 after loosening a restraining knob and screw means 38. Block 30 engages rail 4 at any position along the upper end 34 thereof. A suitable number of safety rings 24 stacked between rail 4 and block 31 prevents side plate 10 from sliding down rail 4 toward the patient, should knob and screw means 38 become accidentally loosened.

As described supra, in FIG. 1, side plate 10 has a slot 40 formed therein. A locking plate 9 includes means (best shown in FIG. 7) to receive a first end of connecting bar 8. The locking plate 9 is connected to side plate 10, at any suitable position along slot 40, by tightening thereto a restraining knob and screw means 42 through slot 40. The position of the first end of connecting bar 8 is otherwise changed by loosening knob and screw means 42 and moving locking plate 9 (in a direction generally indicated by arrow E) to the desired position along slot 40. Knob and screw means 42 is tightened through slot 40 to locking plate 9 to secure plate 9 and, thus, the first end of bar 8 in the desired position.

Figure 7:
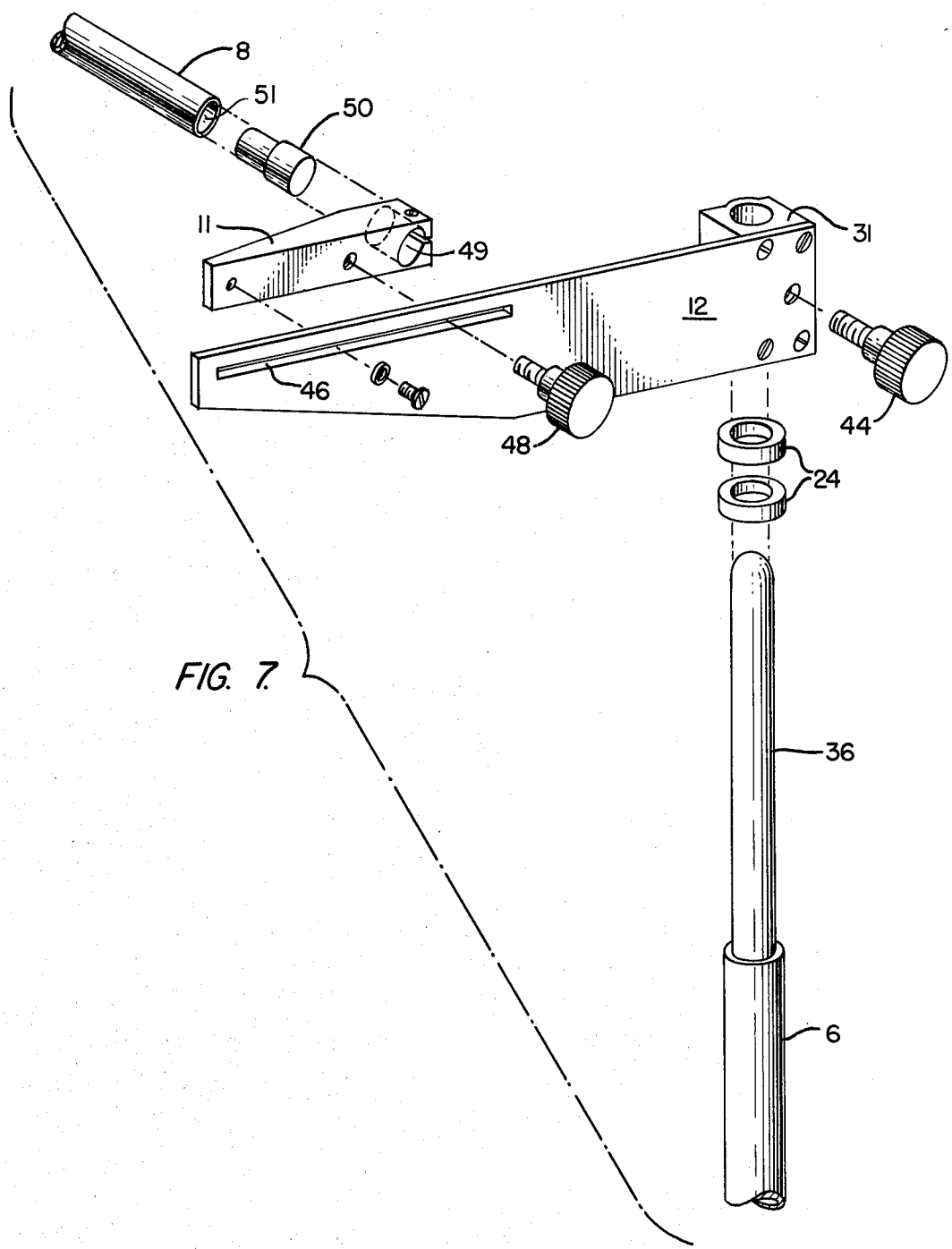

FIG. 7 is a detailed showing of the assembly of side plate 12 with support rail 6 and connecting bar 8. The upper end 36 of support rail 6 is also tapered. As described in FIG. 6, safety rings 24 are stacked along the upper end 6 of support rail 36. The safety rings 24 help to maintain the height (corresponding to that of side plate 10 on support rail 4 of FIG. 6) and prevent slippage of side plate 12 toward a patient. As previously disclosed, side plate 12 has attached thereto block 31 which has an aperture therein adapted to receive the upper end 36 of support rail 6. By loosening a restraining knob and screw means 44, the headholder assembly is adapted to pivot about the upper end 36 of support rail 6 and out of the way of a patient.

As described supra, in FIG. 1, side plate 12 has a slot 46 formed therein. A locking plate 11 includes an opening 49 to receive one end of a suitable spacer 50. Spacer 50 is connected from the opening 49 in locking plate 11 to a sleeve portion 51 formed in the other end of connecting bar 8 (opposite to the first end thereby connected to locking plate 9). However, sleeve portion 51 may be formed in either or both ends of bar 8. The length of spacer 50 may be varied to regulate the distance between the side plates 10 and 12 and thereby adjust the width of the headholder assembly to conform to the width of any patient accomodating means. The locking plate 11 is connected to side plate 12, at any suitable position along slot 46, by tightening thereto a restraining knob and screw means 48 through slot 46. The position of the other end of connecting bar 8 is otherwise changed (to correspond with that of the first end thereof) by loosening knob and screw means 48 and moving locking plate 11 to the desired position along slot 46. Knob and screw means 48 is tightened through slot 46 to locking plate 9 to secure plate 11 and, thus, the other end of bar 8 in the desired position.

It will be apparent that while a preferred embodiment of the invention has been shown and described, various modifications and changes may be made without departing from the true spirit and scope of the invention.

Having thus set forth a preferred embodiment of the instant invention, what is claimed is:

1. In combination:
   first and second support arms,
   connecting means extended between said support arms,
   an elongated member having attached to one end thereof means adapted to fit a portion of a human head,
   clamping means having means by which to receive said connecting means and said elongated member in substantially perpendicular directions with respect to one another,
   means to respectively join each end of said connecting means to said first and second support arms
   at least one end of said connecting means having a sleeve portion formed therein, and
   spacer means,
   said spacer means connected between said sleeve portion and said means to join so as to selectively vary the length of said connecting means between said first and second support arms.

2. An assembly for supporting and positioning a human head, said assembly comprising:
   first and second support arms, each of said support arms having a respective slot formed therein,
   connecting means extending between said support arms at the slots formed therein,
   an elongated member having attached to one end thereof means adapted to fit a portion of the human head,
   clamping means having openings to receive said connecting means and said elongated member in substantially perpendicular directions with respect to one another,
   means by which to change the position of said connecting means along said slots formed in said support arms to thereby move said head fitting means relative to the position of the head, and
   space means received by said connecting means to selectively vary the length of said connecting means so as to adjust the distance between said first and second support arms.

3. The combination recited in claim 2, wherein said clamping means includes restraining means to selectively secure the position of said clamping means at a point along said connecting means,
   said restraining means adapted to be adjusted in order to change the position of said clamping means to a location along the length of said connecting means.

4. The assembly recited in claim 2, including first and second legs,
   means to pivotably engage a first of said first and second support arms to a first of said and second legs, and
   means to removably engage the second of said first and second support arms to the second of said first and second legs,
   whereby said first and second support arms and said connecting means are adapted to be pivoted around the first of said first and second legs.

5. The assembly recited in claim 4, wherein a portion of each of said first and second legs is tapered,
   the tapered portion of said first and second legs engaged to said first and second support arms, and
   means fitted over the tapered portion of each of said first and second legs to provide support for said first and second support arms.

6. The assembly recited in claim 5, wherein said means fitted over the tapered portion of said first and second legs is at least one ring means.

7. The assembly recited in claim 2, including first and second foot means,
   said first foot means connected at one end thereof to one of said first and second legs, and
   said second foot means connected at one end thereof to the other of said first and second legs,
   said first and second foot means providing support for said first and second legs.

8. The assembly recited in claim 7, including means to adjust the length of said first and second foot means.

* * * * *